United States Patent [19]
Hunter

[11] 3,963,031
[45] June 15, 1976

[54] JUNCTURE-LUBRICATED NEEDLE-SUTURE COMBINATION

[75] Inventor: Alastair W. Hunter, Somerville, N.J.

[73] Assignee: Ethicon, Inc., Somerville, N.J.

[22] Filed: Dec. 11, 1974

[21] Appl. No.: 531,561

[52] U.S. Cl. .................................. 128/339; 163/1
[51] Int. Cl.² ........................................ A61B 17/06
[58] Field of Search ..................... 128/335.5, 339; 223/102; 163/1, 5

[56] References Cited
UNITED STATES PATENTS

| 2,193,188 | 3/1940 | Bradley | 128/335.5 |
| 2,814,296 | 11/1957 | Everett | 128/339 |
| 2,928,395 | 3/1960 | Forbes et al. | 128/335.5 |
| 3,394,704 | 7/1968 | Dery | 128/339 |
| 3,799,169 | 3/1974 | Beroff et al. | 128/339 |
| 3,875,946 | 4/1975 | Duncan | 128/339 |

*Primary Examiner*—Dalton L. Truluck
*Attorney, Agent, or Firm*—W. R. Eberhardt

[57] ABSTRACT

A needle-suture combination is provided in which a lubricant layer is provided at the juncture between the needle and the suture and specifically between the inner surfaces of a recess in the blunt end of the needle and the outer surface of one tip of the suture which is inserted into the recess and in tight engagement with at least a portion of the inner surface of the recess. The lubricant lowers the pull-out value of the needle-suture combination.

9 Claims, 3 Drawing Figures

JUNCTURE-LUBRICATED NEEDLE-SUTURE COMBINATION

BACKGROUND OF THE INVENTION

1. Field of the Invention

This invention relates to the field of surgical sutures, and more particularly to the novel needle-suture combinations of the swaged variety in which a lubricant is provided at the juncture of the needle and suture.

2. Description of Prior Art

In the swaging of surgical needles, it has been the practice in the art to strive for maximum holding power in the swaged junction. Minimum requirements for attachment of eyeless needles to absorbable surgical sutures or to non-absorbable surgical sutures is prescribed in the *U.S. Pharmacopoeia*, Vol. XVIII, Page 944 (also see *U.S. Pharmacopoeia*, Vol. XVII, Page 919). It has been the practice of suture manufactures in the United States and abroad to securely attach the suture to the needle by swaging so that the minimum pull-out standard recited in the *U.S. Pharmacopoeia* is met or exceeded.

More recently, there has been developed a needle-suture combination in which pull-out value, i.e., the force required to separate the needle from the suture, are deliberately controlled within the range of 3 to 26 ounces even though such values may be less than minimum values recited in the *U.S. Pharmacopoeia*. These needle-suture combinations are designed to have sufficient pull-out force to prevent accidental separation during use, and yet enable the surgeon to remove the needle at will by a deliberate tug.

Needle-suture combinations having low pullout values may be prepared by controlling the degree of compression during swaging, as disclosed in copending and co-assigned application U.S. Ser. No. 409,974 filed Oct. 26, 1973, now U.S. Pat. No. 3,890,975, issued June 24, 1975. The pull-out value of a conventional needle-suture combination may also be reduced by partially withdrawing the suture from the needle as disclosed in co-pending and co-assigned application U.S. Ser. No. 446,174 filed Feb. 27, 1974, now U.S. Pat. No. 3,875,946, issued Apr. 8, 1975.

The present invention provides a means whereby the pull-out value of any swaged needle-suture combination may be reduced by a small but significant, incremental amount.

SUMMARY

In accordance with the instant invention, the pull-out value of a swaged needle-suture combination is incrementally reduced by providing a lubricant layer between the surfaces of the needle and the suture within the swaged portion of the needle. The lubricant may be applied to the inner surface of the needle hole, or the outer surface of the suture tip, or both, prior to insertion of the suture into the needle recess and swaging. Such needle-suture combinations are characterized by an average suture pull-out value substantially lower than the average force obtained in the absence of the lubricant layer.

DESCRIPTION OF DRAWINGS

In FIGS. 1 and 2, the thickness of the lubricant layers are exaggerated for clarity.

DESCRIPTION OF PREFERRED EMBODIMENTS

Figure 1:
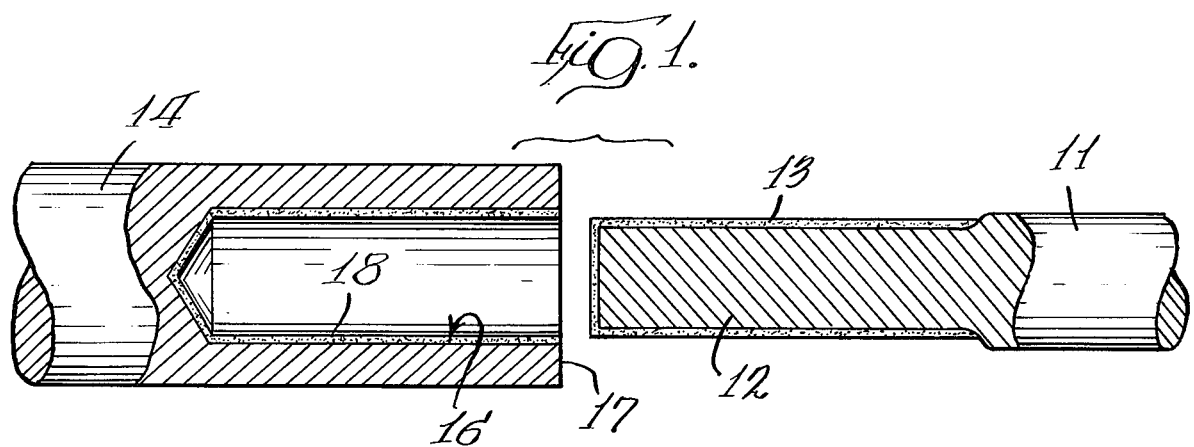
FIG. 1 is an enlarged elevation, partly in cross section, of the blunt end of a drilled needle and the suture end in position to be inserted therein.

In accordance with the present invention, a needle-suture combination having a reduced pull-out value is obtained by coating one end of a suture with a layer of a lubricant material, inserting the lubricated end of the suture into the opening of a drilled needle or channel needle having a lubricant layer on the inner surface of the opening and swaging the needle to tight and holding contact with the suture end. While either the suture tip or the inner surface of the needle opening alone may be coated with a lubricant, it is preferred for best results that both surfaces be coated. The same or different lubricants may be used in coating the needle and the suture where both are coated.

In the manufacture of needle-suture combinations from multifilament suture strands, e.g., braided or twisted strands, the suture is preferably resin tipped to unify the ends and prevent brooming which interferes with needle attachment. Tipping may be accomplished by impregnating a short portion of the suture with a resin in accordance with known techniques and cutting the suture at the place of impregnation to yield a length of suture resin tipped on both ends. Resin tipped ends of multifilament sutures are usually of smaller diameter than the remainder of the suture, as represented by the suture end of FIG. 1. Monofilament sutures which are single unitary structures require no special treatment prior to applying the lubricant and swaging.

Deliberate application of a lubricant layer to the inner surface of the suture recess in the blunt end of a drilled or channel needle in accordance with the present invention is a complete departure from present practice where this surface is maintained free of lubricant. In the manufacture of unlubricated needles, the suture recess is inherently lubricant free. In the manufacture of lubricated needles, where a coating of lubricant is applied to the outer surface of the needle, extreme care is generally taken to avoid getting any lubricant into any portion of the hole in the blunt end.

In the practice of the present invention, the interior of the needle opening may be lubricated by any convenient method. In the case of drilled needles, the needle is conveniently immersed into a bath of lubricant in a volatile liquid carrier and a vacuum is applied to draw the lubricant containing liquid into the hole. When the needle is removed from the bath, a lubricant plug remains in the hole. The volatile carrier is then dried off leaving a lubricant coating on both the outer and inner surfaces of the needle.

The suture tip may be coated with a lubricant layer by any convenient method as for example by dipping the end of the suture into a lubricant in a volatile liquid carrier and then drying off the liquid carrier.

The present invention is applicable to any suture material including for example the absorbable materials, i.e., catgut, extruded collagen, and homopolymers and copolymers of lactide and glycolide; and non-absorbable materials, i.e., silk, nylon, polyproplene, cotton, linen and polyester.

The invention will become more readily apparent upon consideration of the following detailed description taken in connection with the accompanying drawings.

As seen in FIG. 1, suture 11 is a multifilament strand which has been resin impregnated to provide a small, unified tip 12. Lubricant layer 13 is an external coating applied over resin impregnated tip 12.

Needle 14 has a hole 16 drilled into its blunt end 17 in an axial direction, the diameter of hole 16 being only slightly larger than the diameter of suture tip 12 so that the latter can be inserted snugly into the hole. The interior surfaces of hole 16 have been previously coated with lubricant layer 18.

Figure 2:
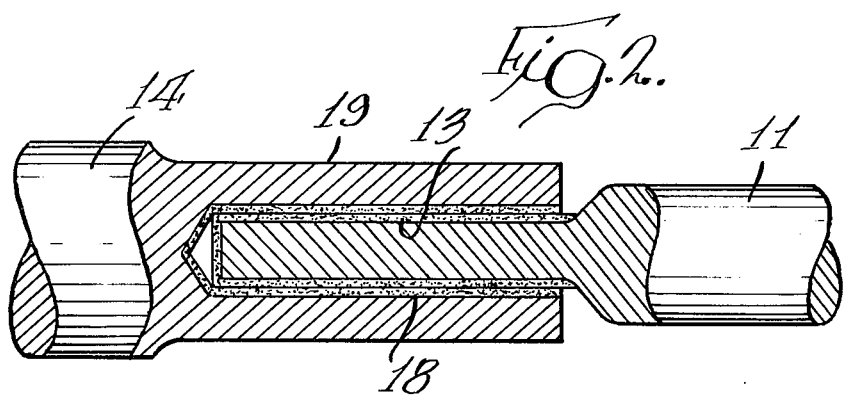
FIG. 2 is an enlarged elevation, partly in cross section of the needle suture juncture of this invention after the suture is inserted into the hole in the blunt end of the needle, and the blunt end is swaged.

FIG. 2 shows the needle-suture juncture after suture 12 is inserted into hole 16 and the blunt end of the needle is swaged to form deformation 19 and to compress tip 12 to a predetermined extent.

Figure 3:
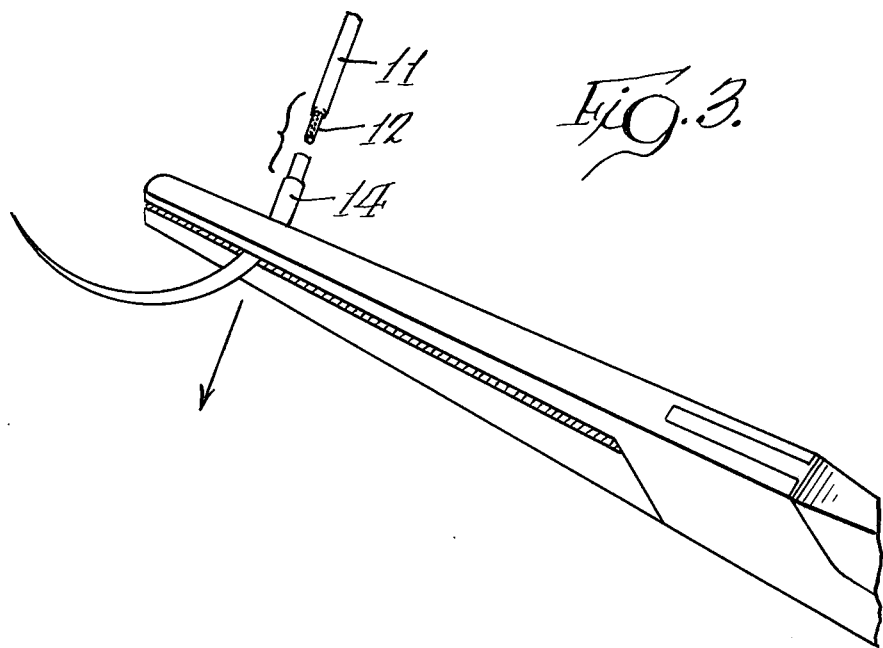
FIG. 3 is a perspective view of the needle-suture combination of the present invention after thhe needle has been separated from the suture.

FIG. 3 shows the needle suture immediately after separation with tip 12 withdrawn from its juncture within the hole at the swaged end of the needle.

Any lubricant material which is non-toxic and capable of depositing a solid, semi-solid or liquid layer of good lubricity may be used in this invention to lubricate the suture tip and to lubricate the interior surface of the recess in the needle. In the preferred embodiment where both the suture tip and the needle recess surfaces are coated with a lubricant, either the same lubricant or different lubricants may be used, as desired. Also, since the exterior needle surfaces are frequently coated with a lubricant layer for easing passage of the needle through tissue, the interior surfaces can be coated with the same lubricant as a matter of convenience.

Suitable lubricant materials include silicone polymers; polyhaloalkylene polymers, particularly polytetrafluoroethylene; polyalkylene glycol polymers such as methoxy polyethylene glycol and polypropylene glycol; polytetramethylene glycol polymers with a molecular weight in the range of from about 2,000 to about 13,000; hydroxyl-terminated polyester polymers from di-acids and glycols such as polytetramethylene adipate polymer; hydroxyl-terminated polyester polymers from the polymerization of lactones in the presence of a polymethylene diol such as polycaprolactone; metallic stearates such as aluminum stearate, calcium stearate and zinc stearate; long chain aliphatic amides such as coconut oil amide, oleamide and stearamide; glycerol esters of long chain fatty acids such as glycerolmono- and distearates, glycerol mono- and dioleates, and glycerol mono- and dilaurates; animal waxes such as spermaceti; insect waxes such as beeswax; vegetable waxes such as carnauba wax, Japan wax and cocoa butter; mineral waxes such as petrolatum, paraffin wax, microcrystalline waxes and montan wax; and polyolefins such a polyethylene dispersions.

The lubricant, as stated above, is conveniently applied from a volatile liquid carrier. The carrier may be a solvent for the lubricant, or the lubricant may be finely dispersed in a non-solvent liquid. Typical carriers, which may be either solvents or non-solvents depending on the nature of the lubricant, include water, hydrocarbons such as n-heptane, benzene and toluene, and halogenated hydrocarbons.

In some cases a lubricant may be used without a carrier, particularly a lubricant which is produced in situ from a monomeric state to a polymeric state, or from an uncured state to a cured state. Some silicone materials are commonly sold and used without a solvent or carrier and can serve in the uncured state as adhesives. They may be cured in situ, however, to produce stable silicone polymer coatings which have lubricant properties.

The invention also contemplates utilization, as a suture tip lubricant, of materials such as waxes which are commonly used to lubricate the entire length of certain suture materials but which are ordinarily removed from the suture tips prior to impregnating the suture tips with a resin, or which are coated over with a resin prior to insertion of the suture tip into needle recesses and swaging. Where a wax-coated silk braided suture, for example, would be soaked at its tip in a solvent for removal of the wax and thereafter impregnated with a resin before insertion into a needle recess and swaging, the present invention contemplates keeping the wax coating on the suture tip as a lubricant, inserting the wax-coated tip into a needle recess (preferably lubricated on its inner surfaces) and then swaging.

The lubrication of only the suture tip has been found to reduce average pull-out values by an average of about 20 percent compared to the average pull-out values for similar systems with an unlubricated suture tip, with a maximum observed pull-out reduction for an individual sample of about 65 percent.

The lubrication of only the inner surfaces of the hole with silicone has been found to reduce average pull-out values by an average of about 15 percent compared to the average pull-out values of similar systems in which the inner surfaces of the hole are unlubricated, with a maximum observed pull-out value reduction for an individual sample of about 65 percent.

When both the suture tip and the inner surfaces of the hole are lubricated, average pull-out values are reduced on the average by about 30 percent compared to the average values for similar systems without lubrication on either the suture tip or the inner surfaces of the hole, with a maximum observed pull-out value reduction for an individual sample of about 75 percent.

EXAMPLES 1 TO 8

Size 2-0 black braided silk sutures were resin impregnated at their tips with a conventional polyester resin tipping solution in preparation for insertion into 0.0187 inch diameter drilled holes in the blunt ends of needles. In Example 1, the control, neither the needle hole nor the suture tip was lubricated. In other examples, either the needle hole, or the suture tip, or both, were lubricated as shown in Table I, below. The blunt ends of the needles were subjected to conventional stake swaging and the pull-out values were determined.

Table I

| Example | Suture Lubricant | Hole Lubricant | Average Pull-Out Value | | Pull-Out Value Range |
|---|---|---|---|---|---|
| | | | (lbs) | (kg) | |
| 1 | none | none | 6.90 | 3.13 | 6.00–7.25 (lbs) 2.72–3.29 (kg) |
| 2 | silicone | none | 5.20 | 2.36 | 3.00–6.25 (lbs) 1.36–2.84 (kg) |
| 3 | polyester | none | 4.30 | 1.95 | 2.50–5.50 (lbs) 1.13–2.50 (kg) |
| 4 | Teflon | none | 5.00 | 2.27 | 2.50–6.25 (lbs) 1.13–2.84 (kg) |
| 5 | none | silicone | 6.50 | 2.95 | 4.50–7.50 (lbs) 2.04–3.40 (kg) |
| 6 | silicone | silicone | 4.40 | 2.00 | 1.75–5.50 (lbs) 0.79–2.50 (kg) |

Table I-continued

| Example | Suture Lubricant | Hole Lubricant | Average Pull-Out Value (lbs) | Average Pull-Out Value (kg) | Pull-Out Value Range |
|---|---|---|---|---|---|
| 7 | polyester | silicone | 4.60 | 2.09 | 2.25–6.00 (lbs) 1.02–2.72 (kg) |
| 8 | Teflon | silicone | 4.50 | 2.04 | 2.75–6.25 (lbs) 1.25–2.84 (kg) |

EXAMPLES 9 TO 16

The procedure of Examples 1 to 8 was repeated, substituting size 2-0 green braided polyethylene terephthalate sutures for the silk sutures.
The results are shown in Table II.

Table II

| Example | Suture Lubricant | Hole Lubricant | Average Pull-Out Value (lbs) | Average Pull-Out Value (kg) | Pull-Out Value Range |
|---|---|---|---|---|---|
| 9 | none | none | 6.60 | 2.99 | 5.50–8.00 (lbs) 2.50–3.63 (kg) |
| 10 | silicone | none | 4.50 | 2.04 | 2.25–6.00 (lbs) 1.02–2.72 (kg) |
| 11 | polyester | none | 4.50 | 2.04 | 3.50–5.50 (lbs) 1.59–2.50 (kg) |
| 12 | Teflon | none | 5.30 | 2.40 | 3.75–6.75 (lbs) 1.70–3.06 (kg) |
| 13 | none | silicone | 5.50 | 2.50 | 3.75–7.25 (lbs) 1.70–3.29 (kg) |
| 14 | silicone | silicone | 4.30 | 1.95 | 2.50–5.75 (lbs) 1.13–2.61 (kg) |
| 15 | polyester | silicone | 4.20 | 1.91 | 3.50–5.50 (lbs) 1.59–2.50 (kg) |
| 16 | Teflon | silicone | 4.60 | 2.09 | 3.00–6.00 (lbs) 1.36–2.72 (kg) |

EXAMPLES 17 TO 24

The procedure of Examples 1 to 8 was repeated, substituting size 2-0 blue polypropylene monofilament sutures for the silk sutures and utilizing round swaging in place of stake swaging. The monofilament sutures were not resin treated prior to application of the lubricant.
The results are shown in Table III.

Table III

| Example | Suture Lubricant | Hole Lubricant | Average Pull-Out Value (lbs) | Average Pull-Out Value (kg) | Pull-Out Value Range |
|---|---|---|---|---|---|
| 17 | none | none | 5.50 | 2.50 | 3.75–7.00 (lbs) 1.70–3.18 (kg) |
| 18 | silicone | none | 5.70 | 2.59 | 4.25–6.75 (lbs) 1.93–3.06 (kg) |
| 19 | polyester | none | 4.80 | 2.18 | 3.50–6.25 (lbs) 1.59–2.84 (kg) |
| 20 | Teflon | none | 5.00 | 2.27 | 3.00–6.25 (lbs) 1.36–2.84 (kg) |
| 21 | none | silicone | 4.40 | 2.00 | 2.50–5.50 (lbs) 1.13–2.50 (kg) |
| 22 | silicone | silicone | 4.70 | 2.13 | 3.00–6.00 (lbs) 1.36–2.72 (kg) |
| 23 | polyester | silicone | 4.40 | 2.00 | 3.25–5.50 (lbs) 1.47–2.50 (kg) |
| 24 | Teflon | silicone | 3.80 | 1.72 | 2.25–5.00 (lbs) 1.02–2.27 (kg) |

EXAMPLES 25 TO 32

The procedure of Examples 17 to 24 was repeated, substituting size 2-0 black nylon monofilament sutures for the polypropylene sutures.
The results are shown in Table IV.

Table IV

| Example | Suture Lubricant | Hole Lubricant | Average Pull-Out Value (lbs) | Average Pull-Out Value (kg) | Pull-Out Value Range |
|---|---|---|---|---|---|
| 25 | none | none | 6.10 | 2.77 | 3.50–8.00 (lbs) 1.59–3.63 (kg) |
| 26 | silicone | none | 4.70 | 2.13 | 3.25–6.50 (lbs) 1.47–2.95 (kg) |
| 27 | polyester | none | 5.20 | 2.36 | 2.50–7.50 (lbs) 1.13–3.40 (kg) |
| 28 | Teflon | none | 4.90 | 2.22 | 3.00–6.75 (lbs) 1.36–3.06 (kg) |
| 29 | none | silicone | 4.90 | 2.22 | 2.00–7.00 (lbs) 0.91–3.18 (kg) |
| 30 | silicone | silicone | 3.90 | 1.77 | 2.50–5.50 (lbs) 1.13–2.50 (kg) |
| 31 | polyester | silicone | 4.50 | 2.04 | 3.00–6.00 (lbs) 1.36–2.72 (kg) |
| 32 | Teflon | silicone | 4.40 | 2.00 | 2.75–6.50 (lbs) 1.25–2.95 (kg) |

In the above examples, the lubricant identified as "polyester" was polytetramethylene adipate which was applied in solution in toluene; the lubricant identified as "silicone" was a polysiloxane which was applied in solution in n-heptane; and the lubricant identified as "Teflon" was a polytetrafluoroethylene which was applied in an aqueous dispersion.

It is to be understood that the foregoing examples are intended to be merely illustrative and that modifications and variations will be apparent to those skilled in the art.

What is claimed is:

1. In a needle-suture combination having a suture pull out value of from about 3–26 ounces comprising a needle having a sharp end and a blunt end, means forming a recess at the blunt end of said needle and a suture having a tip at one end positioned within said recess, said blunt end being swaged to bring at least a portion of the inner surfaces of said recess into tight engagement with said suture tip to attach said suture to said needle, the improvement comprising having a lubricant layer between said suture tip and said inner surface of said recess in an amount effective to substantially reduce the suture pull-out value relative to the pull-out value in the absence of said lubricant layer.

2. A needle-suture combination of claim 1 wherein said recess is a drilled hole.

3. A needle-suture combination of claim 1 wherein said recess is a channel.

4. A needle-suture combination of claim 1 wherein said suture is a multifilament suture.

5. A needle-suture combination of claim 4 wherein said suture is a braid.

6. A needle-suture combination of claim 1 wherein said suture is selected from the group consisting of catgut, extruded collagen, homopolymers and copolymers of lactide and glycolide, silk, nylon, polypropylene, polyester, cotton and linen.

7. A needle-suture combination of claim 1 wherein said suture is a monofilament.

8. A needle-suture combination of claim 1 wherein said lubricant layer comprises separate layers applied to said inner surface and to said suture tip prior to said swaging.

9. A needle-suture combination of claim 1 wherein said lubricant layer is selected from the group consisting of polytetrafluoroethylene, polysiloxane, polytetramethylene adipate, and combinations thereof.

* * * * *